United States Patent [19]

Morimoto et al.

[11] Patent Number: 5,056,962
[45] Date of Patent: Oct. 15, 1991

[54] METHOD OF SAMPLING SOLID MATERIALS AND SAMPLING SYSTEM TO EXECUTE THE METHOD

[75] Inventors: Kiyoshi Morimoto, Mishima; Akikazu Iwamoto; Katsuya Watanabe, both of Sunto; Masahiko Shimizu, Mishima; Masuo Moriyama, Numazu, all of Japan

[73] Assignee: Kyowa Hakko Kogyo Co., Ltd. Kabushiki Kaisha Matsui Seisakusho, Osaka, Japan

[21] Appl. No.: 457,248

[22] Filed: Dec. 27, 1989

[30] Foreign Application Priority Data

Dec. 27, 1988 [JP] Japan .................. 63-332432
Nov. 8, 1989 [JP] Japan .................. 1-290883

[51] Int. Cl.⁵ .................................. B65G 53/66
[52] U.S. Cl. ............................. 406/49; 406/13; 406/14; 406/50
[58] Field of Search .......... 406/13, 14, 49, 56, 406/111, 151, 197, 50

[56] References Cited

U.S. PATENT DOCUMENTS 2,763,446  9/1956  Hanson ........................... 406/13
4,856,941  8/1989  Morimoto et al. ........... 406/49
4,941,777  7/1990  Kieronski ..................... 406/13

FOREIGN PATENT DOCUMENTS 0828623  12/1986  U.S.S.R. ......................... 406/49

Primary Examiner—Sherman Basinger
Assistant Examiner—Virna Lissi Mojica
Attorney, Agent, or Firm—Koda and Androlia

[57] ABSTRACT

A method and the related system for sampling solid materials. Materials as continuously manufactured from a compression molding machine are sampled at fixed intervals and the materials thus sampled are fed into a transport pipe so as to be transferred by being accompanied by a transport plug into an inspecting station at low speed from its stand-by position in the pipe when a gas control means is set in a feed mode. After transferring sampled materials the transport plug left at its terminal position in the transport pipe is automatically returned to the stand-by position through the transport pipe when the gas control means is set in a suction mode. By executing the above steps repeatedly, sampled materials are successively transferred into the inspecting station by being accompanied by the transport plug under unmanned operation.

5 Claims, 10 Drawing Sheets

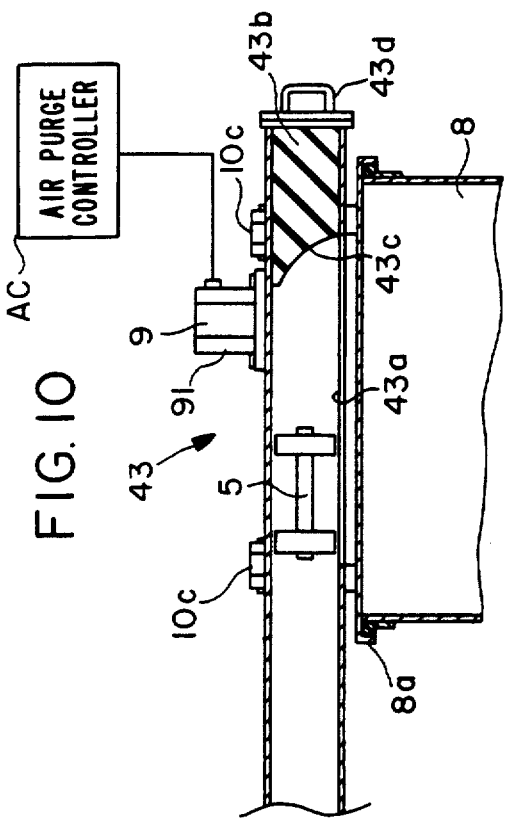
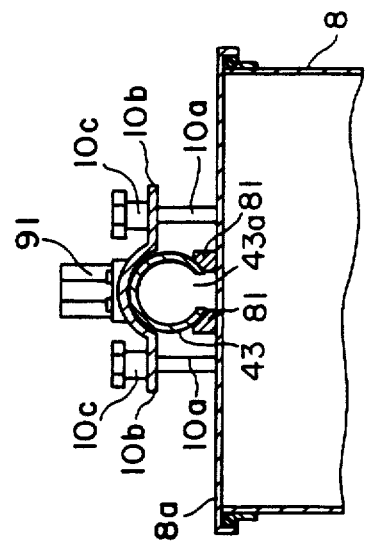
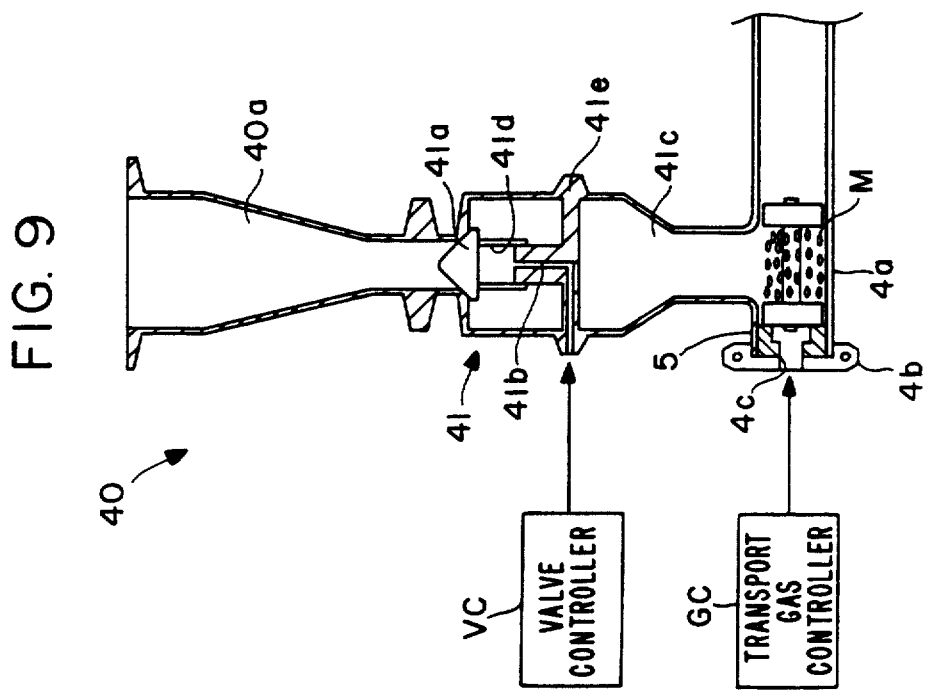

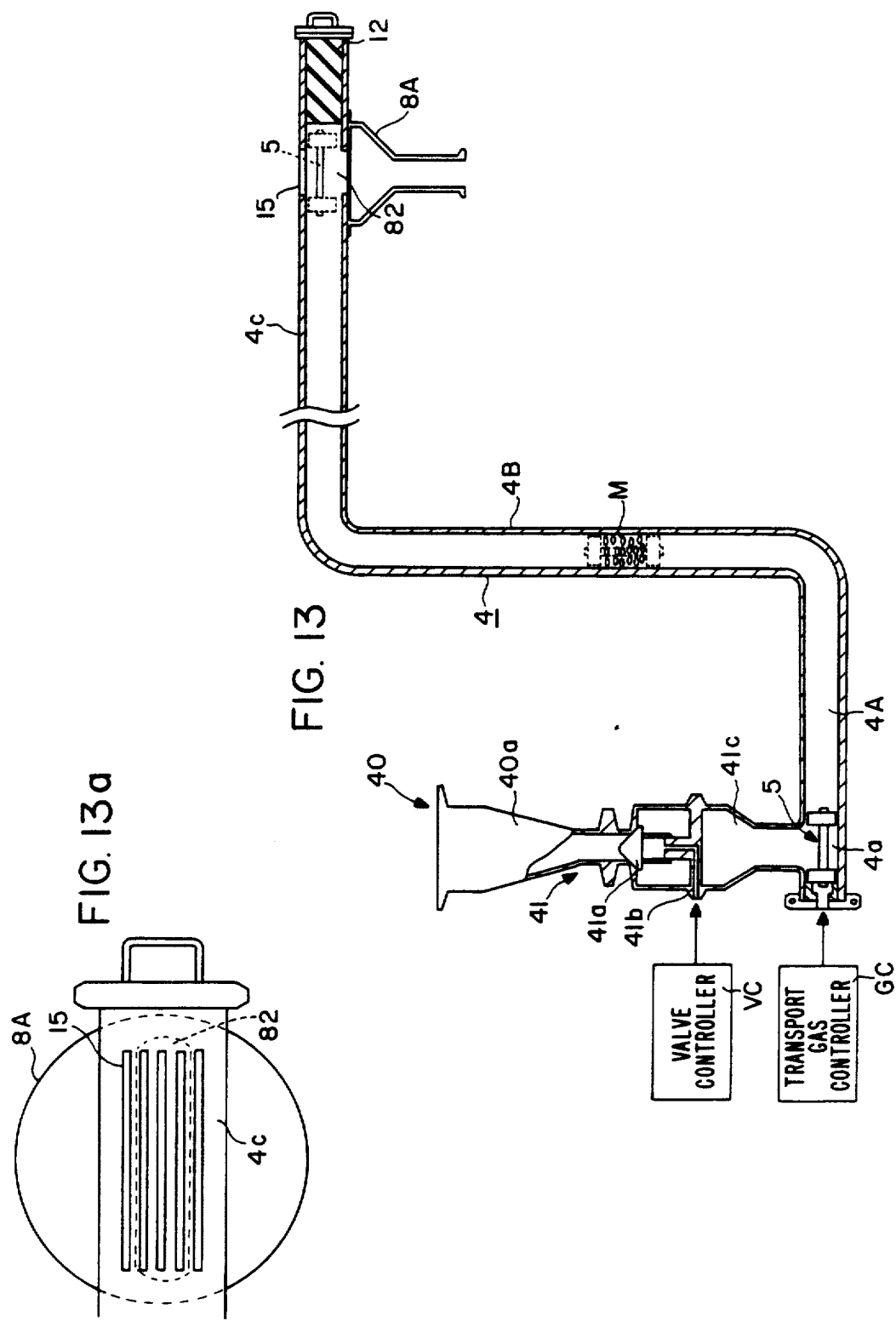

METHOD OF SAMPLING SOLID MATERIALS AND SAMPLING SYSTEM TO EXECUTE THE METHOD

BACKGROUND OF THE INVENTION

1. Field of the Invention

The present invention relates to a method for automatically transferring sampled solid materials such as medical tablets to an inspecting station by low-speed pneumatic transportation for a quality inspection and the like and a new sampling system to execute the same.

2. Prior Art

As to certain solid materials especially medical tablets for example, it is indispensable to execute random sampling at fixed intervals to check the quality of manufactured tablets after the tablets are manufactured continuously at high speed by a tablet molding machine. And conventionally an inspector executes such a sampling inspection at regular intervals (for example every 10–30 minutes).

However, nowadays a new automatic sampling system adapted to be disposed adjacent to the tablet molding machine has been developed wherein tablets are counted and weighed automatically and the numbers and weight are recorded to itself.

Moreover, a tablet molding machine constructed to be washable with water on the spot has been also developed and its maintenance and examination have become more convenient.

However, in the case of washing off such a molding machine with water, it would be very troublesome to transfer the inspection unit by the side. And since a balance scale is housed in the inspection unit, the unit would be badly affected by the vibration of tablet molding machine when disposed adjacent to the machine. Actually, these problems have become more important nowadays.

Moreover, sampling of medical tablets is required to be executed directly by an inspector who is in charge of quality control other than those who are concerned with manufacturing of tablets in a plant. Therefore, there would be a possibility to cause dust and to be contaminated with foreign materials.

Considering the above mentioned problems, a new sampling method of solid materials proposed by the present inventors has been disclosed in Japanese Patent Application No. 63-332432 wherein sampled materials are transported at low speed and at high density. It is an practical method because it can be fully executed under unmanned factory system, has no requirement to move and place the tablet molding machine by the side in case of maintenance and examination, and moreover doesn't give an impact on sampled materials to cause crack or chip.

SUMMARY OF THE INVENTION

The present invention is directed to provide a preferable sampling method for tablets wherein sampling work can be done under unmanned operation, the tablet molding machine need not be moved and placed by the side during maintenance and examination, the tablets do not receive an impact to cause crack or chip and also directed to provide a sampling system to execute the method effectively.

A first method according to the present invention to achieve above mentioned objects, comprises the following steps; feeding a fixed amount of solid materials as continuously manufactured from a compression molding machine into a transport pipe for sampling; transferring a fixed amount of solid materials thus sampled into an inspecting station by pneumatically transporting a transport plug at low speed in the transport pipe from its stand-by position in the pipe by use of pressurized gas; and after completion of transportation of the sampled materials accompanied by the transport plug, returning only the transport plug left at a terminal position in the transport pipe to the stand-by position through the transport pipe by suction operation.

A first system simultaneously proposed according to the present invention, comprises a sampling/feeding means to sample solid materials as continuously manufactured by a compression molding machine at fixed intervals and to feed sampled materials; a transport gas control means to transport sampled materials by executing either a feed or a suction mode; a transport pipe having an inlet to receive sampled materials from the sampling/feeding means and connected to the transport gas control means at the initial end thereof and to a material receiver of an inspecting station at its terminal end; and a transport plug disposed at initial end side of the sampling inlet in the pipe, as a stand-by position, the plug being pneumatically transported together with the sampled materials at low speed into a terminal position in proximity to the inspecting station from the stand-by position when the gas control means is set in a feed mode, and then being returned to the stand-by position from the terminal position after being transferred into the terminal position in the pipe when the gas control means is set in a suction mode.

A second method according to the present invention comprises the following steps; feeding a fixed amount of solid materials as continuously manufactured from a compression molding machine into a transport pipe for sampling; transferring a fixed amount of solid materials thus sampled into an inspecting station by pneumatically transporting a transport plug at low speed in the transport pipe from its stand-by position in the pipe by use of pressurized gas; and after completion of transportation of sampled materials accompanied by the transport plug, injecting pressurized gas from the end of the transport pipe toward its initial end, with the initial end side of a terminal position of the plug open to atmosphere, whereby the transport plug is returned to the stand-by position in the transport pipe.

A second system according to the present invention comprises; a sampling/feeding means to sample solid materials as continuously manufactured by a material supply station such as a compression molding machine at fixed intervals and to feed the sampled materials into a transport pipe; a transport pipe having an inlet to receive sampled materials from the sampling/feeding means and connected to a material receiver of an inspecting station at its terminal end; a gas control means to supply transport gas into the transport pipe; a means to open the transport pipe into atmosphere, provided at initial end side of the plug housing portion constituting a stand-by position of the transport plug; a means to inject pressurized gas provided at terminal end side of the terminal position of transport plug in the transport pipe; and a transport plug disposed in the housing portion in the transport pipe, the plug being pneumatically transferred together with said sampled materials at low speed into the terminal position thereof in the transport pipe by transport gas supplied from initial end of the pipe after receiving sampled materials, and being returned to the stand-by position by driving the means to inject pressurized gas after being transferred into the terminal position in the pipe.

And a system is constructed such that degassing holes are further provided at the upper wall of the end of transport pipe connected to the material receiver whereby excess gas is bled to atmosphere before sampled materials are received into the receiver.

Now functions to be achieved by the present invention will be explained below.

According to the present invention, since the transport plug transfers sampled materials taken out after being manufactured at the molding machine to the inspecting station at low speed by the use of pressurized gas in the transport pipe and is thereafter suck and returned to the first stand-by position, one transport plug can transfer sampled materials repeatedly at low speed.

And according to the present invention, as a manufacturing station of compression moldings and the inspecting station of sampled materials are connected by the transport pipe, the inspecting station can be installed apart from the manufacturing station. Therefore, it becomes unnecessary for an inspector to go to the manufacturing place each time for sampling and further the problems such as dust and contamination of foreign materials which are apt to cause can be solved.

Furthermore, according to the present invention, the inspecting station is not affected by the vibration of manufacturing station and does not become an obstacle in case of maintenance and examination of manufacturing station. And, since sampled materials taken out after being manufactured into tablets are transferred to the inspecting station at low speed by the transport plug through the transport pipe and the transport plug is forcibly returned to the first stand-by position by injecting pressurized gas after finishing transferring, sampled materials can be transferred to the inspecting station repeatedly by one transport plug.

Especially according to the present system, initial end side of the stand-by position of transport plug in the transport pipe is opened after the transport plug reaches the terminal position in the pipe and finishes the transportation, at this moment pressurized gas has almost no resistance to go through from the end to the leading end of the transport pipe. And then, pressurized gas is injected in the reverse direction of transportation, and as a result, the transport plug is made to be transferred smoothly through the transport pipe and to be returned swiftly to the stand-by position at the leading end thereof.

According to the present system, a fixed amount of solid materials continuously supplied by the material supply station such as a compression molding machine is sampled and provided into the transport pipe, then the sampled materials are transferred into the inspecting station in such a manner that a transport plug disposed at the sand-by position in the transport pipe is transferred by pressurized gas through the pipe at low speed, then after finishing transferring, the plug left at the terminal position in the pipe is returned to the first stand-by position through the pipe. At this time, according to the present invention, the leading end of the transport pipe is opened and the plug is forcibly returned to the first stand-by position by injecting pressurized gas from the end of the pipe.

According to the present system, since transport gas is bled into atmosphere through degassing holes formed in the upper wall of transport pipe connected to the material receiver when sampled materials are transported into the inspecting station, measuring errors caused by being applied extra transport gas to a measuring unit housed in the material receiver can be prevented.

BRIEF DESCRIPTION OF THE DRAWINGS

FIG.1 is a schematic block diagram showing a basic construction of a first system;

FIG. 2 shows one embodiment of a transport plug;

FIG. 3 illustrates an insert port for sampling;

FIG. 4 is a block diagram showing a basic construction of the other embodiment according to the first system;

FIG.5 is a diagram showing an embodiment of a means to control transport gas;

FIG.6 is a flow chart showing a control process of the present invention.

FIG.7 through FIG.13 illustrate a second system of the present invention;

FIG.7 is a schematic block diagram showing a basic construction of a second system;

FIG.8 is a perspective view when a second system is applied to the transport system for medical tablets;

FIG. 9 illustrates the construction of a sampling inlet;

FIG. 10 shows the construction of a plug receiving portion of material receiver;

FIG. 11 is a transverse sectional view of FIG. 10;

FIG. 12 shows the construction of the other embodiment of a transport pipe at the terminal end connected to an inspecting station;

FIG. 13 illustrates the construction of the other embodiment of the present system;

FIG. 13a is a plain view of the terminal end of transport pipe showing degassing holes.

DETAILED DESCRIPTION OF PREFERRED EMBODIMENT

Now more detailed descriptions will be given referring to drawings.

At first, a first method and the related system according to the present invention will be explained.

Figure 1:
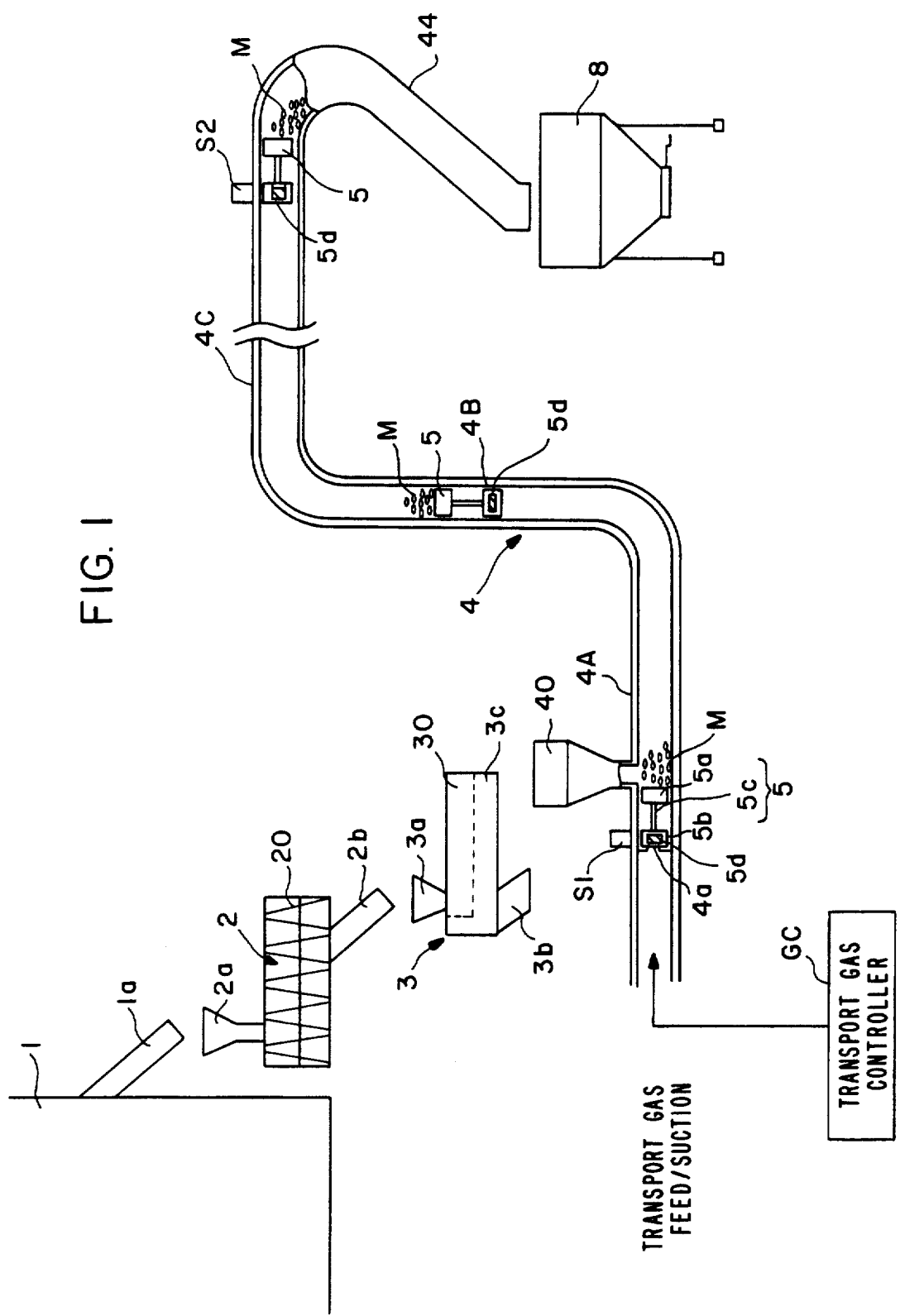
FIG. 1 through FIG. 6 illustrate a first system according to the present invention.

FIG. 1 shows the construction of basic system according to the first invention.

A fixed amount of medical tablets M as continuously manufactured by a tablet molding machine 1 is taken out at fixed intervals from a sample outlet 1a of the tablet molding machine 1 and then stored in the main body 20 of a powder eliminator 2 through a sample inlet 2a thereof. After excess powder is removed in the eliminator 2, tablets are supplied into a vibrating feeder 3 from a discharge outlet 2b passing through a hopper 3a. The medical tablets M supplied from the hopper 3a are discharged from an outlet 3c of the vibrating feeder 3 by driving a electromagnetic vibrator 3b installed under the feeder 3 to vibrate a trough 30 and are contained in a transport pipe 4 through a sampling inlet 40 thereof.

In this embodiment, tablet molding machine 1 constitutes a sampling/feeding means, but any other construction can be employed.

As a transport plug 5 is disposed at a stand-by position which is initial end side of the sampling inlet 40 in the transport pipe 4, the medical tablets M inserted from the sampling inlet 40 are placed in a space ahead of a front body 5a of the plug 5. And when a gas control means GC is set in a feed mode and transport gas is supplied into the transport pipe 4 from a gas source, the transport plug 5 carries medical tablets M forward by the pressure.

According to the present invention, transport gas is settled so as to transfer the transport plug 5 under pressure at low speed. Therefore, sampled tablets M may be transferred in the transport pipe 4 without receiving any impact, stopped at the terminal position in the transport pipe 4, and then contained in a material receiver 8 provided at inspecting station. The tablets M thus sampled and transferred are counted and weighed by means of a material measuring unit (not illustrated) disposed in the material receiver 8 of inspecting station.

Accordingly, when the transportation of sampled tablets M is completed, the gas control means GC is set in a suction mode and the transport plug 5 left at the terminal position in the transport pipe 4 is suck and returned to the first stand-by position for next transportation. Numerals S1 and S2 indicate sensors to detect a stand-by position and a terminal position of transport plug 5 respectively. According to the system shown in FIG.1, the gas control means GC is automatically switched corresponding to the detection signals from two sensors S1 and S2.

The transport pipe 4 of the present system, as shown in FIG.1, is constructed such that a lower horizontal pipe 4A having the sampling inlet 40 is connected to a vertical riser pipe 4B, the riser pipe 4B is connected to an upper horizontal pipe 4C, and the terminal end of upper pipe 4C is connected to a discharge pipe 44 gently inclined downwardly toward the material receiver 8 of inspecting station. Of course the construction of transport pipe is not limited to this embodiment.

However, when materials are adapted to be transferred upwardly in the vertical riser pipe 4B at low speed by the transport plug 5, the above mentioned construction of transport pipe is preferable to prevent crack or chip of materials because the materials are kept from touching the internal surface of pipe 4 while being transferred therein.

Further, in the present invention, it is preferable to use a transport plug 5 which is able to transport all of the sampled tablets M when transferring in the transport pipe 4.

Figure 2:
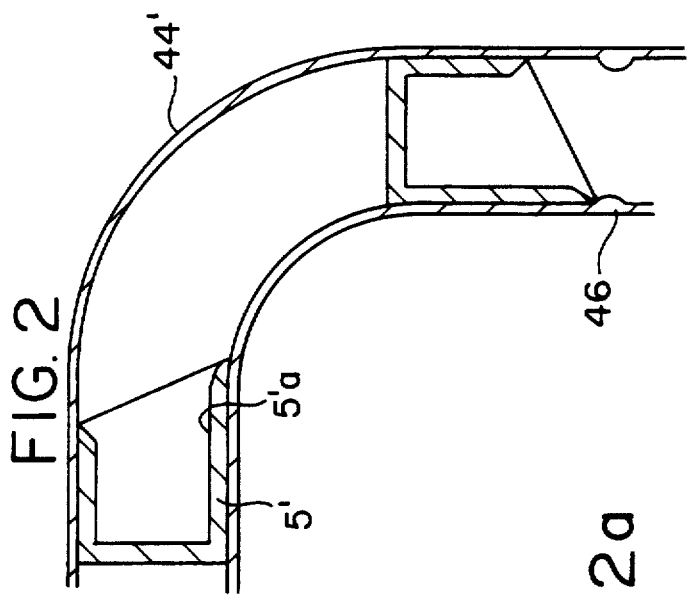
Figure 2A:
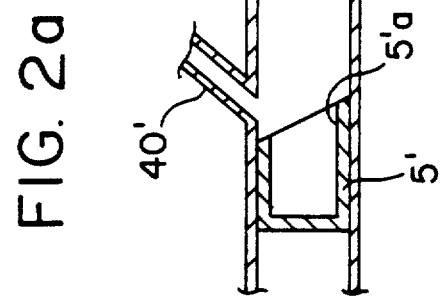
FIG. 2a illustrates the construction of the leading end of a transport pipe.

As an example of the above mentioned transport plug, FIG. 2 illustrates a cylindrical plug 5' having a container portion 5'a of which open end is obliquely cut. When such a plug is employed, it is preferable that instead of the sampling inlet 40 as described above, an inclined pipe 40' to insert samples as illustrated in FIG. 2a is provided at the leading end of transport pipe 4 from where sampled tablets M are inserted into the container portion 5'a of cylindrical plug 5'a.

FIG.2 illustrates the transport plug 5 at the terminal position in the transport pipe 4. The plug 5 is stopped by a convex portion 46 provided as a stopper at the terminal position in the transport pipe 4.

According to the present invention, the transport plug 5 is required to wait for an insert of a fixed amount of medical tablets kept at the stand-by position in the transport pipe 4 before transferring the tablets and to be kept in the terminal position in the pipe 4 after finishing the transfer. For this purpose, an embodiment illustrated in FIG.1 is constructed such that a magnetic material 5d is contained in the rear body 5b of transport plug 5, sensors S1 and S2 employed with magnets are provided at the stand-by position and the terminal position respectively in transport pipe 4 to detect those positions, so that the transport plug 5 can stop at each position by magnetic force. However, the plug is not limited to this construction.

Figure 3:
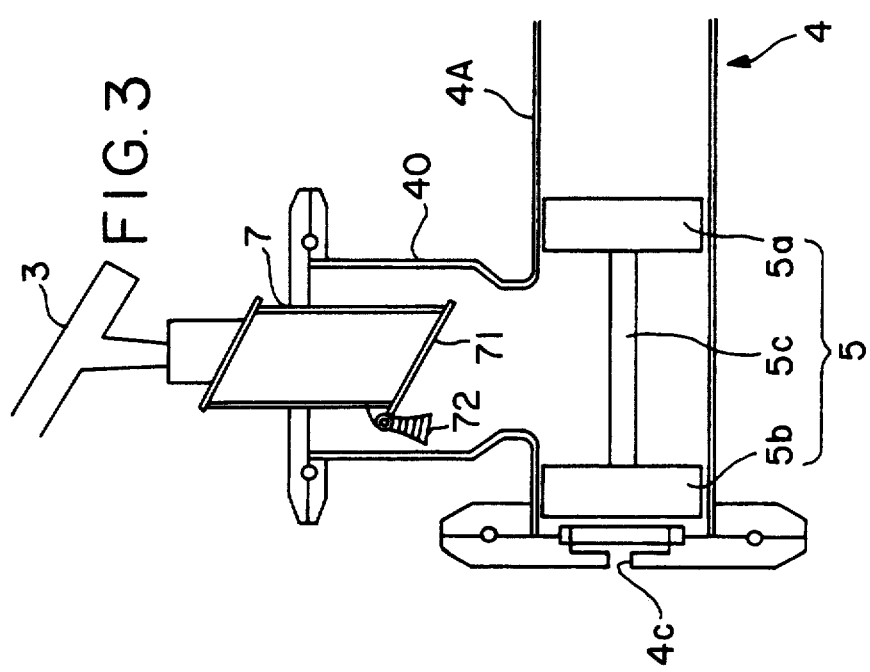

FIG.3 illustrates more concrete construction of the sampling inlet 40 provided at the initial portion of transport pipe 4. In this embodiment, combination of the sampling inlet and tablet molding machine constitute a sampling/feeding means. A receiving cylinder 7 of which bottom is provided with a damper 71 having a balance weight 72 is installed in the sampling inlet 40 employed at the horizontal pipe 4A of transport pipe 4 and the transport plug 5 is disposed closely under the damper 71. In FIG.3, the transport plug 5 is constructed such that the front body 5a and the rear body 5b elastically attached to the inner surface of transport pipe 4 are connected by a shaft 5C. Unlike the embodiment of FIG.1, sampled tablets M are contained in the space between the front body 5a and the rear body 5b and transferred through the transport pipe 4.

Further in this embodiment, the initial end of transport pipe 4 has a small opening 4c to introduce transport gas and the caliber thereof is formed smaller than that of the rear body 5b of transport plug 5 so as to be used as a stopper when the plug 5 is suck and returned.

According to such a construction, since the receiving cylinder 7 having the balance weight 72 is opened when the medical tablets weighing more than the balance weight 72 are inserted, sampled tablets M which are less than the fixed amount may not be transferred to the inspecting station.

Further in the present invention, it is preferable that the caliber of transport pipe 4 corresponding to the terminal position of transport plug 5 is formed smaller than that of the body of transport plug 5 in order to keep the plug 5 at the terminal position and is also preferable that the caliber of pipe 4 is gradually tapered so as not to give an impact on medical tablets. Therefore, it isn't necessary to contain a permanent magnet in the body of transport plug 5 thereby the construction can be simplified.

Figure 4:
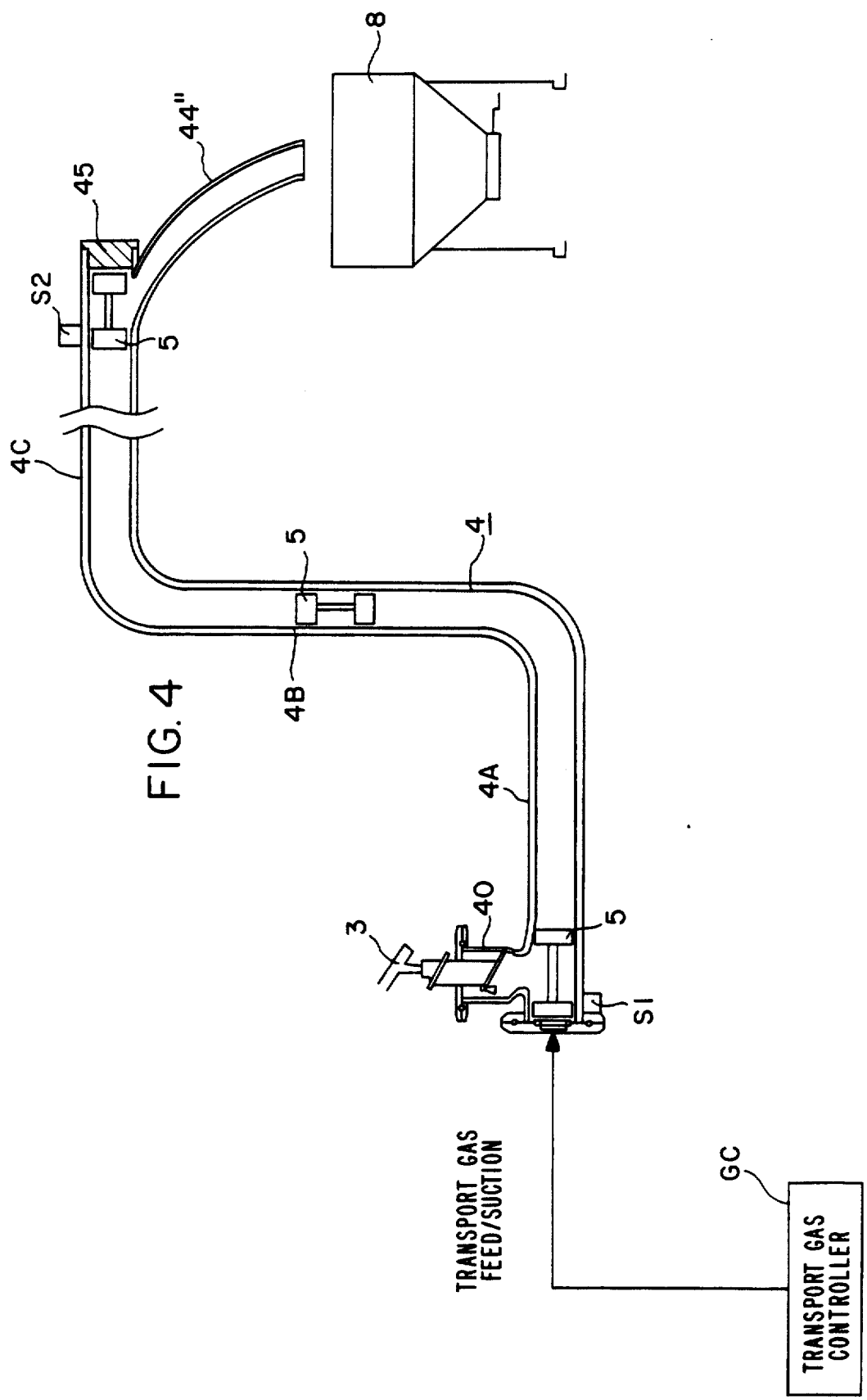

FIG.4 shows the other embodiment of the first invention wherein sampled materials kept in the space between the front body 5a and the rear body 5b of transport plug 5 are transferred. The system is constructed such that the sampling inlet 40 is the same as the one illustrated in FIG.3, the transport pipe 4 has a gently inclined discharge pipe 44" in order to stop the transport plug 5 at the terminal position when the plug 5 reaches the end portion of pipe 4, sampled materials fall through the pipe 44", thus stored in the receiver 8 of inspecting station.

Figure 5:
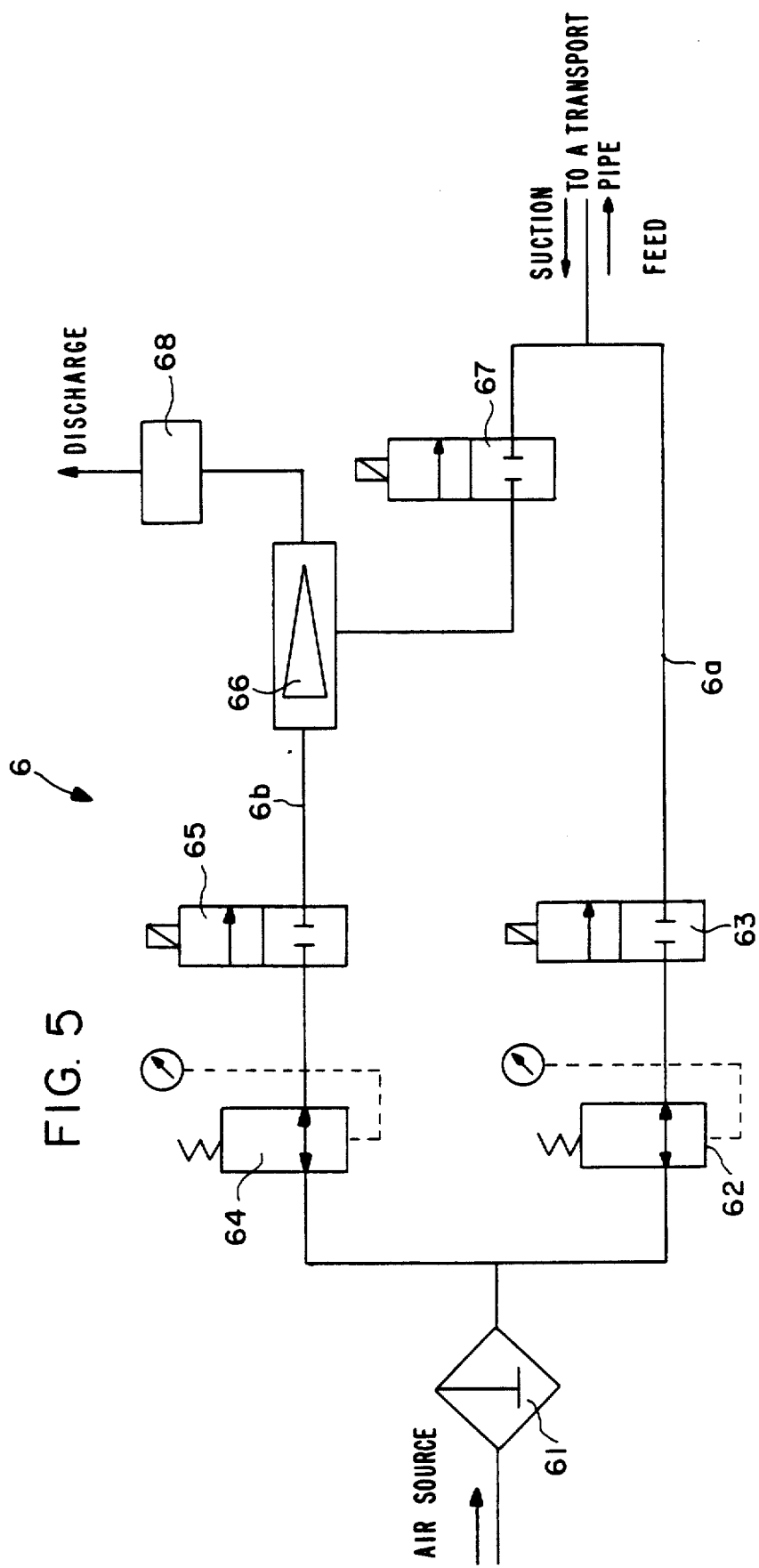

FIG.5 illustrates the construction of transport gas control means GC according to the first invention.

The gas control means GC is connected to an air source (not illustrated) through a filter 61 from where two gas feed pipes (lines) 6a and 6b are branched. The pipe 6a feeds pressurized gas into the transport pipe 4 and has a regulator 62 which adjusts the feeding pressure of the gas and an electromagnetic control valve 63 which controls open and close operation of the pipe 6a. The other pipe 6b is a suction line having a regulator 64 and an electromagnetic control valve 65 which function the same as those for the pipe 6a and connected to the transport pipe 4 through the suction inlet of an ejector 66 and an electromagnetic control valve 67. The discharge outlet of ejector 66 is open to atmosphere through a silencer 68.

According to the transport gas control means GC as mentioned above, the means is set in a feed mode and then pressurized gas is fed to the transport pipe 4 when the air source is driven to cause the electromagnetic valve 63 open. The means is set in a suction mode and then the gas in the transport pipe 4 is suck by the working of ejector 66 when the electromagnetic valve 63 is closed and simultaneously the electromagnetic valve 64 and 65 are opened.

Figure 6:
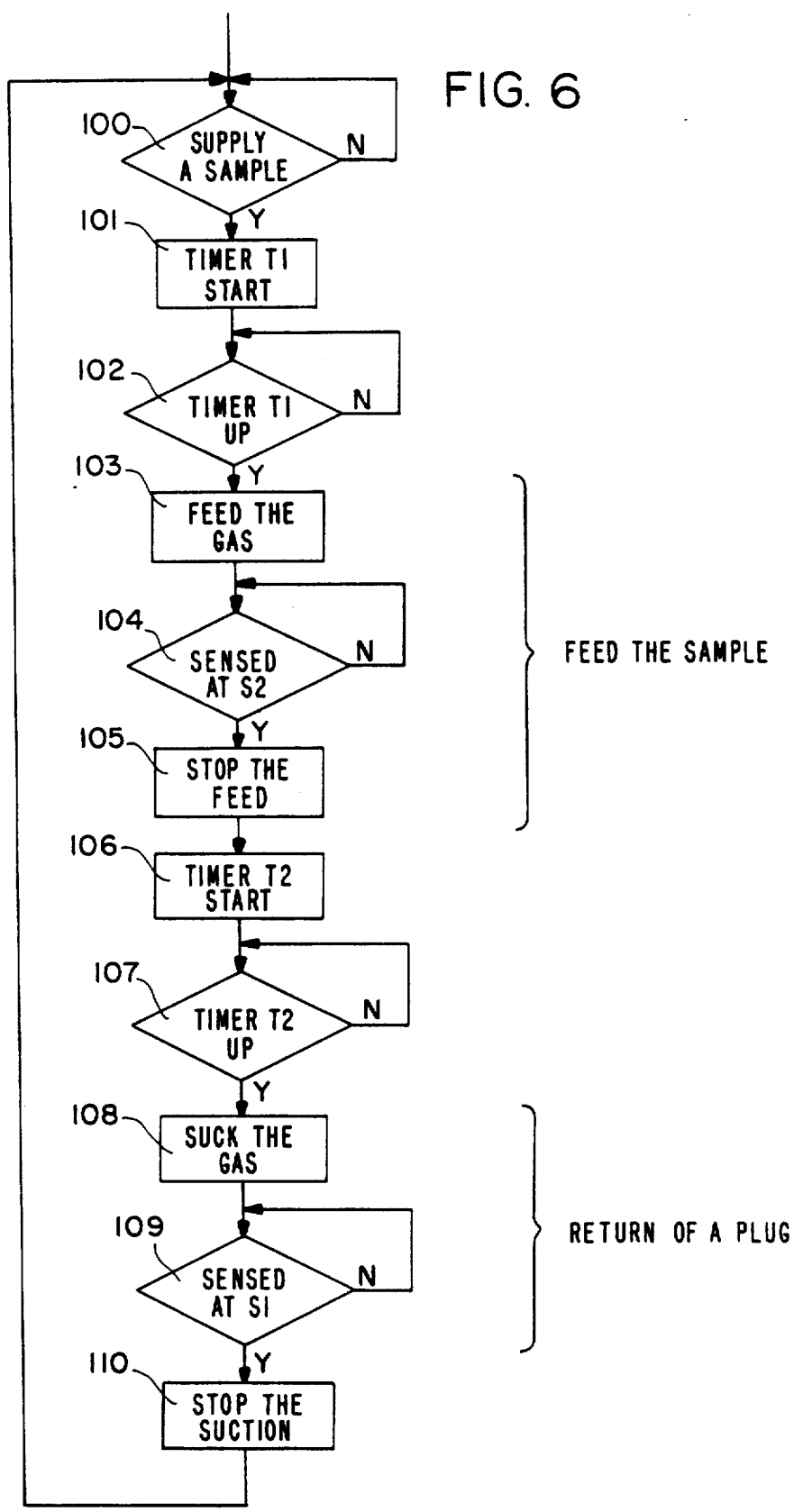

The steps 100–110 of FIG.6 show a flow chart of control operation of the above mentioned control means. A timer T1 provides the time needed for charging of a fixed amount of sampled materials in the transport pipe 4. A timer T2 provides the time needed for arrival of all the transferred sampled materials at the material receiver 8.

Now a second system of the present invention will be given.

Figure 8:
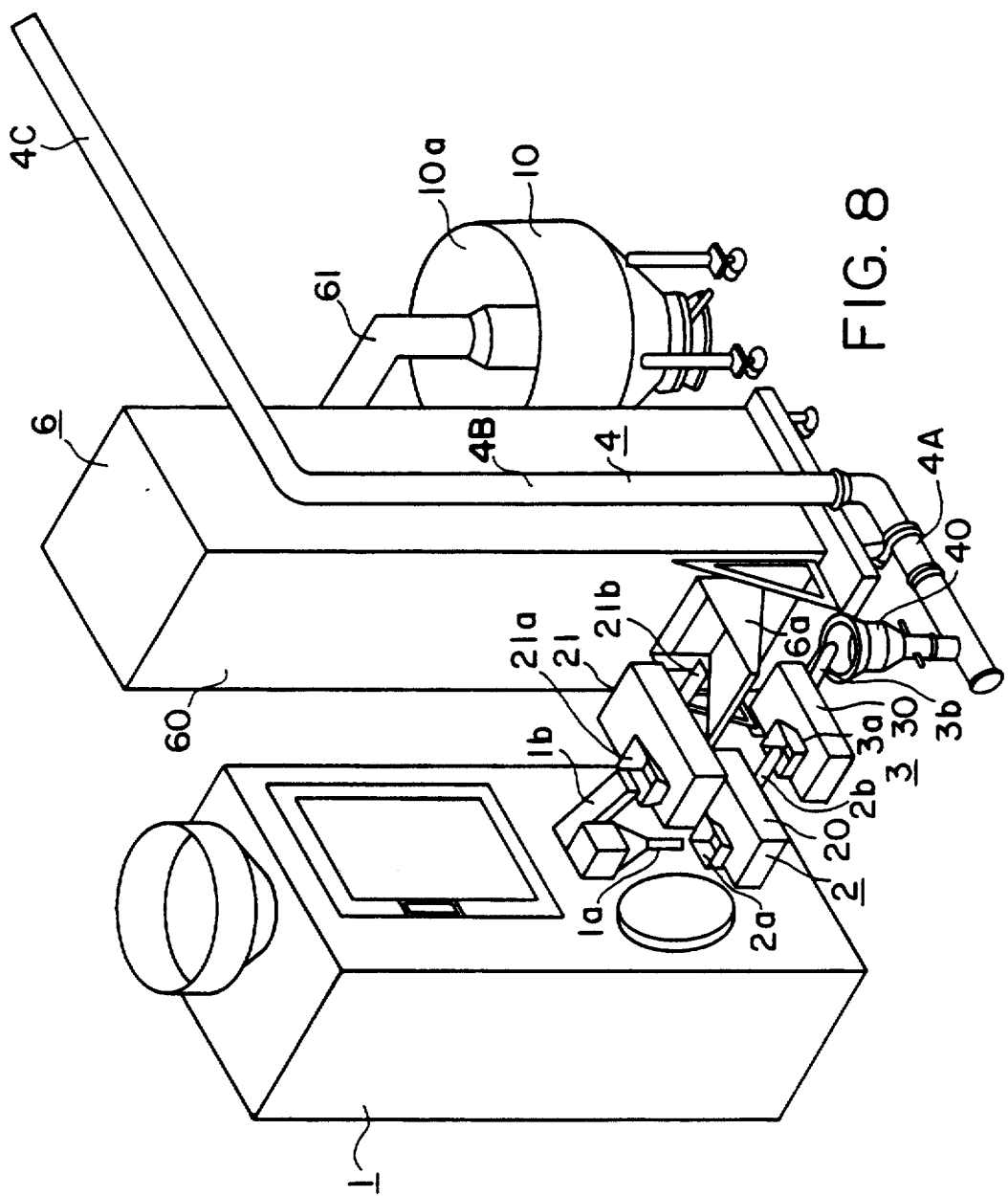

FIG. 8 shows a diagram of a basic system when the second system is applied to the transportation of sampled tablets.

A tablet molding machine 1 has exposed take-out ports 1a and 1b in the front thereof, as shown in FIG.8. The numeral 1a indicates a take-out port for sampling and 1 indicates a main take-out port.

The medical tablets continuously manufactured in the main body of tablet molding machine 1 are taken out successively from the port 1b, fed to a powder eliminator 21 through a feed port 21a, discharged from an outlet 21b, and supplied to a tablet transferring unit 6 containing an elevating system. The materials are supplied through a front hopper 6a into the unit 6, carried upwardly by a bucket conveyer (not illustrated) and fed into a tank 10a of a carrier container 10 through a discharge port 61 provided on the rear of unit 6. The carrier container 10 is carried to a next station for other treatment and the materials thus manufactured are successively carried into the next station.

On the other hand, a fixed amount of materials is taken out for random sampling at fixed intervals from the port 1a which is one of the take-out ports comprising the material take-out means of tablet molding machine 1, stored in the main body 20 of powder eliminator 2 through a receiving port 2a thereof, discharged from an outlet 2b, and fed into a vibrating feeder 3 through a hopper 3a. The sampled materials are discharged from an outlet 3b by driving an electromagnetic vibrator (not illustrated) to cause the main body 30 of feeder 3 to vibrate and fed into the transport pipe 4 through a sampling inlet 40.

Figure 7:
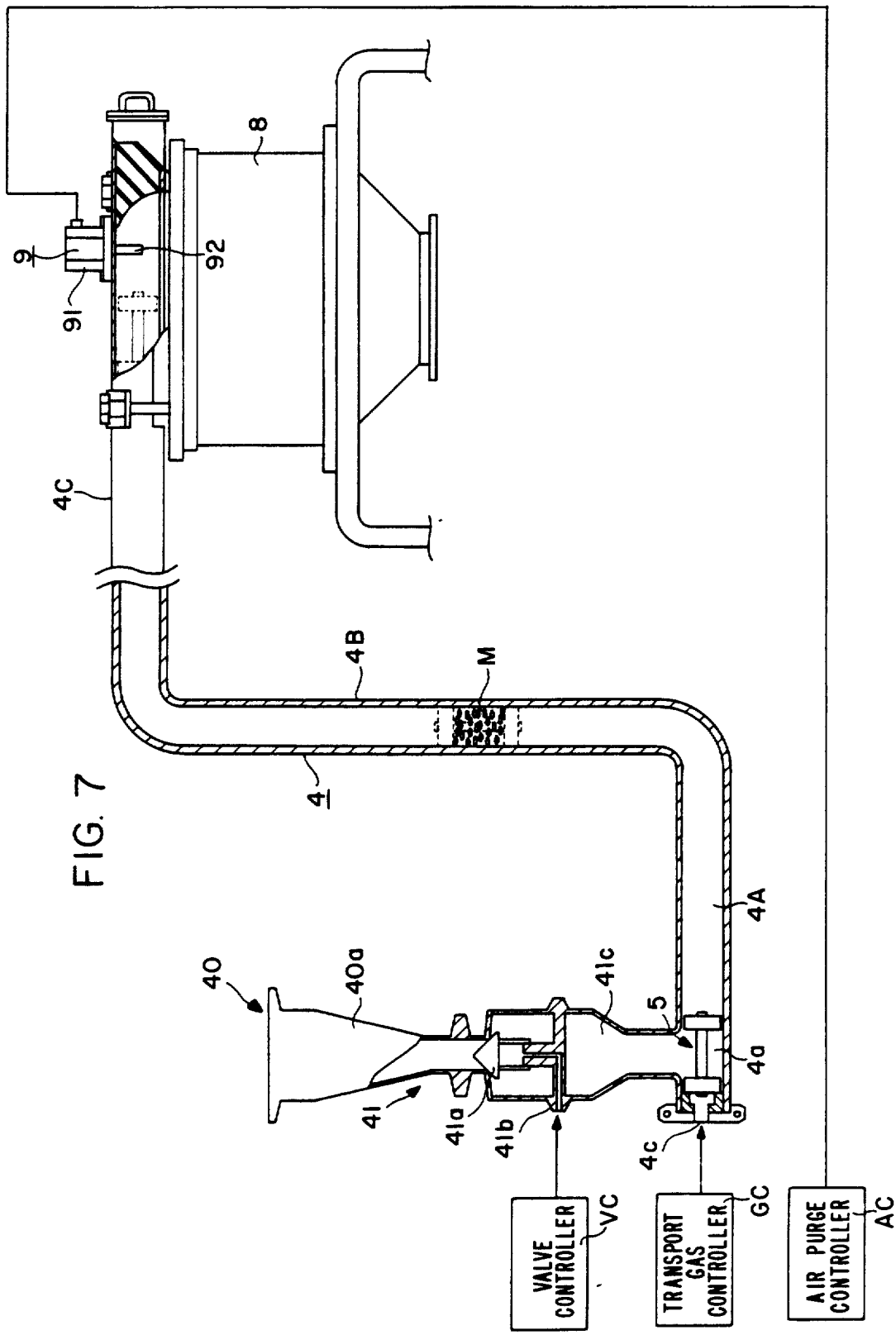

The transport pipe 4 has the inlet 40 to receive sampled materials from the feeder 3 and a housing portion 4a for a transport plugs at the initial end thereof. In FIG.7, the housing portion 4a is formed under a valve 41 of inlet 40, which forms a stand-by position.

The transport pipe 4, as shown in FIGS.7 & 8, is constructed such that a first horizontal pipe 4A is connected to a vertical riser pipe 4B, the end of riser pipe 4B is connected to a second horizontal pipe 4C and extended to the inspecting station, wherein the end of the pipe 4 is connected with a material receiver 8. In this embodiment, though a conic valve 41 provided at the sampling inlet 40 is used as a means to open to atmosphere, another valve may be provided at initial end side of the stand-by position of transport plug 5 in the transport pipe 4.

FIG.9 shows the construction of sampling inlet 40, according to the construction, the conic valve 41 is opened by lowering a valve head 41a thereof when the sampled materials are fed into the transport pipe 4 and when after the feeding of the sampled materials is completed, it is closed by lifting the valve head 41a. The conic valve 41 is disposed under a tapered receiving cylinder 40a and provided with a housing 41c having the valve head 41a. In the housing 40c, a T-shaped shaft 41e having a branch pipe which forms a passage 41b to introduce pressurized air by a valve control means VC is provided and the branch pipe of shaft 41e is put with a cylindrical body 41d fixed at the bottom of valve head 41a. When the pressurized air is supplied from the valve control means VC, the valve head 41a is lifted by the pressure of air and the receiving cylinder 40a is closed. While, when the means VC stops the air supply, pressurized air leaks from the clearance between the cylindrical body 41d and the branch pipe of shaft 41e and the valve head 41a falls down by gravity to cause the valve 41 to open.

The sampling inlet 40 is provided with the plug housing portion 4a thereunder in the transport pipe 4, wherein the transport plug 5 is housed as its stand-by position. The numeral 4b indicates a stopper to specify the stand-by position of plug 5 in the pipe 4 and 4c is a port to feed pressurized gas supplied from the transport gas control means GC.

The stand-by position and the terminal position of transport plug 5 are detected by sensors (not illustrated). The sensors send signals to a control panel in order to open and close the conic valve 41 and in order to control a gas injection means 9, described hereafter.

As shown in FIGS. 10 & 11, the material receiver 8 disposed at the inspecting station side is connected to a plug receiving portion 43 at the end of second horizontal pipe 4c of transport pipe 4 and the lower wall of the receiving portion 43 is formed with a rectangular opening 43a of which width is formed smaller than the diameter of transport plug 5 to pass falling materials. The receiving portion 43 is placed on a seat frame 81 surrounding the rectangular opening 43a formed with a rid 8a of the receiver 8 fixed airtightly in such manner that each two hold-down metals 10b is threaded through a bolt 10a embedded at the rid 8a so as to cover the receiving portion 43a and is fastened with a knob 10c. And a padding plug 43b having a guide surface 43c forming a circular arc is padded at the opening end of plug receiving portion 43 so that materials can smoothly fall into the receiver 8 without receiving an impact from the surface 43c. Further, the padding plug 43b is inserted to be removable and has a handle 43d to facilitate maintenance. But it is fixed airtightly with a clamp band 43d normally.

FIGS. 7 & 10 show the gas injection means 9 as employed with an air purge unit 91 at end side of the terminal position of transport plug 5 in the transport pipe 4, that means forward periphery of the padding plug 43b of plug receiving portion 43.

The air purge unit 91 is comprised of a main body provided with a projectable cylinder 92 having a gas injection outlet. The cylinder 92 is housed in the inner wall of transport pipe 4 so as not to interrupt the material transportation when an air purge control means AC is not driven (see FIGS. 10 & 11). While, when pressurized gas is supplied by driving the air purge control means AC, the cylinder 92 is in turn projected from the inner wall to inject pressurized gas into the leading end of the transport pipe 4. Such material receiver 8 and pressurized gas injection means 9 as described above can be used for the first system, wherein the transport plug 5 transfers sampled materials into the inspecting station when the gas control means GC is set in a feed mode, then returns to the first stand-by position when set in a suction mode. In order to return the transport plug 5 smoothly, it is necessary to stop the plug 5 short of the opening 43a (initial end side in the transport pipe 4) after completing material transportation and to operate the pressurized gas injection means 9 for fine adjustment.

Next, control procedures of the second method are explained hereinafter referring to FIGS. 7 & 8.

When a fixed amount of medical tablets are inserted into the receiving cylinder 40a of sampling inlet 41 through the powder eliminator 20 and the feeder 3 by opening the sample take-out port 1a of tablet molding machine 1, the valve control means VC stops feeding pressurized gas to lower the valve head 41a down to open the valve so that the materials stored in the cylinder 40a fall downward through the housing 41c. After completion of that operation, the valve control means VC is activated to lift the head 41a and as a result material supply is stopped. The materials thus fallen into the transport pipe are, as shown in FIG.7, charged in the space between the bodies 5a and 5b, since the transport plug 5 which is constituted of the front and the rear body 5a and 5b and a shaft 4c connecting therebetween is located under the valve head 41a.

After the materials are charged in the space, pressurized gas is fed from the opening 4c provided at the initial end of transport pipe 4 by operating the gas control means GC and the plug 5 is carried forward in the pipe 4 by the pressure of gas. As a result, the plug 5 accompanied by the material is carried forward in the transport pipe by the pressure of gas, and then is transferred into the inspecting station through the first horizontal pipe 4A, the vertical riser pipe 4B and the second horizontal pipe 4C.

The present system is constructed such that pressurized transport gas is set so as to transport the plug 5 in the pipe 4 at low speed and that further increased air resistance in the vertical pipe 4B enables the plug 5 to reduce the transporting speed. Accordingly, the sampled materials M may be transferred upwardly in the vertical riser pipe 4B and transferred into the inspecting station without receiving any impact. When the plug 5 accompanied by the materials reaches the terminal position in the pipe 4, i.e. the opening 43a of plug receiving portion 43, it stops by losing the pushing force because of the leakage of pressurized gas from the opening 43a. Then the materials M transferred by the plug 5 are collected in the receiver 8 in the form of free fall for inspection.

After the transportation of materials M completes, the valve control means VC stops its operation to cause the conic valve 41 to open to atmosphere again by lowering the valve head 41a. Simultaneously the air purge control means AC is activated and the cylinder 92 of air purge unit 91 is projected into the inside of pipe 4 from the inner wall thereof to inject pressurized gas into the initial end of pipe 4, it means into the plug 5. As a result, the plug 5 which has completed the transportation of materials M is forcibly returned to the stand-by position moving smoothly through the pipe 4. Unlike the transportation of materials, the plug 5 is returned swiftly because there is no fear to break or crack. In this way, the transport plug 5 is placed at the stand-by position to prepare next transportation of sampled materials.

FIGS. 1 & 7 show the preferred embodiment of transport pipe 4 according to the present invention, wherein the first horizontal pipe 4A having the sampling inlet 40 is connected to the vertical riser pipe 4B and further to the second horizontal pipe 4C of which end the material receiver 8 of inspecting station 8 is provided, whereas the transport pipe is not limited to this construction. However, when the transport plug 5 is adapted to transfer materials in a vertical riser pipe at low speed, unlike in a horizontal pipe the materials are prevented from touching the inner surface of the pipe while transporting since the materials' own weight is supported by the plug 5, so that such a construction is preferable to keep materials from breaking and cracking.

The transport plug 5 to be used in the present invention is required to be able to transport all of the sampled materials M. Cylindrical plug like a cup having a containing portion of which opening end is obliquely cut may be used as one of examples.

And the transport plug 5 is required to be disposed at its stand-by position in the pipe 4 waiting for the insert of a fixed amount of materials M before transferring and be disposed in the terminal position after finishing transferring. For this purpose, the plug 5 may be constructed such that a magnetic material is contained in the rear body 5b of plug 5, a sensor having magnet is provided at the stand-by position and the terminal position in the pipe 4 respectively to detect those positions, and by which magnetic forces the plug 5 can stop at each position. Whereas, the construction is not limited to the above mentioned.

According to the present invention, to house the plug 5 at the terminal position, the caliber of pipe 4 may be formed gradually tapered so as not to give an impact on sampled materials M and the caliber corresponding to the terminal position of plug 5 may be formed smaller than that of the plug 5. Such a transport pipe need not be embedded with a permanent magnet in the body of plug 5, thus simplifying the construction.

Figure 12:
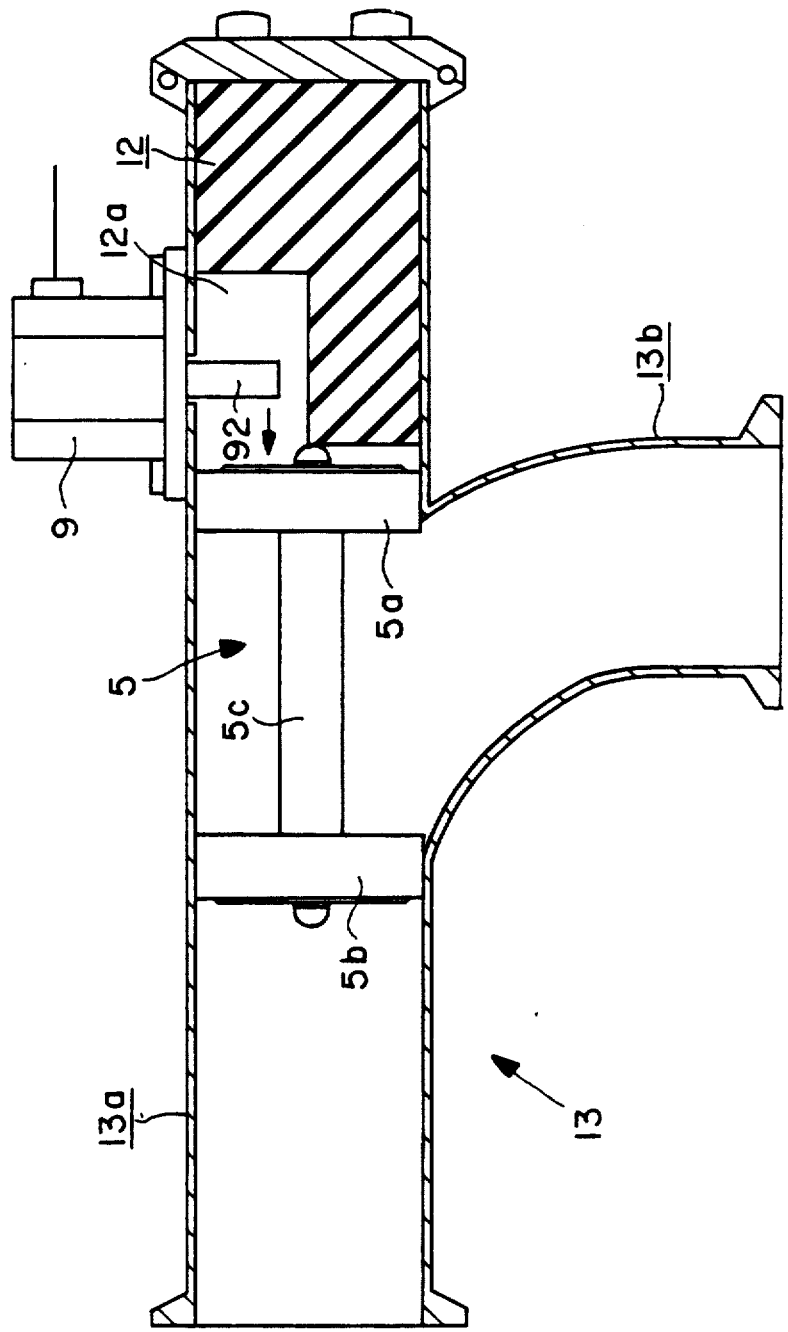

As shown in FIG.12, the inspecting station may be connected with an elbow pipe 13 instead of the material receiver 8 wherein the elbow pipe 13 has a branch pipe 13b extended downwardly with a gentle curve from one end of a straight pipe 13a of which another end is equipped with a blind cap 12. And a material receiver (not illustrated) may be installed under the branch pipe 13b of elbow pipe 13.

According to such a construction, the transport plug 5 stops at the blind cap 12 provided at the end of straight pipe 13a, then sampled materials M stored between the front and rear body 5a and 5b of plug 5 fall down through the branch pipe 13b. After all materials M fall down, the cylinder 92 of air purge unit 91 is projected to a cutout 12a at the top of blind cap 12 to inject pressurized gas in a direction of initial end of the pipe 4 (shown as an arrow), thus enables the plug 5 to return to the stand-by position in the pipe 4, like the foregoing embodiment.

In FIG.13, a plurality of degassing holes 15 formed like slits are provided, enlarged details are shown in FIG. 13a, above the end of pipe 4 connected with a material receiver 8A, which has an opening 82 to fall material M transferred by the plug 5. A measuring unit (not illustrated) is disposed directly under the receiver 8.

According to such a construction, transport gas fed by the gas control means GC is bled to atmosphere through the degassing holes 15 after transporting sampled materials by pushing the plug 5. As a result, there is no fear that excess gas enters the receiver 8 together with the materials and causes measuring errors by applying extra pressure on the measuring unit, thus sample measuring of high accuracy can be obtained in addition to the above-mentioned effects.

Though the air purge unit is not illustrated in FIG.13, it is needles to say that it is provided to make the transport plug forcibly return by purging air.

As is apparent from the above mentioned explanation, following effects can be obtained by the present invention.

In each present method since a manufacturing station of compressed moldings and an inspecting station of sampled materials are connected by a transport pipe 4, they can be installed separately in the same area. Therefore, an inspector needs not go to the manufacturing place each time of sampling and moreover the problems such as dust and contamination of foreign goods can be solved.

Especially according to the second method, since the-transport plug 5 returns by pressurized gas injected from the terminal end of transport pipe 4, the suction method is unnecessary. Therefore, a closed transportation of simple construction can be realized, wherein sampled materials M are transferred being trapped in the pipe 4 without causing any breakage and crack.

Further, according to the first and the second system the inspecting station is not affected by the vibration of manufacturing station nor becomes an obstacle for maintenance and examination of the manufacturing station.

Especially according to the second system, a sampling system can be simplified as the suction means is unnecessary to return the plug 5 and can make it possible to pneumatically transport sampled materials M at low speed. Further, a means for opening to atmosphere disposed at initial end side of a plug housing portion can be shared by the valve 41 provided at the sampling inlet 40. Therefore, a sampling system of much simplified construction can be realized by adding a pressurized gas injection means at the terminal end of the transport pipe 4.

Moreover, according to the sampling system, a measuring unit disposed in a material receiver 8 is adapted not to be pressurized by excess transport gas, so that a sampling system without causing measuring errors can be provided.

What is claimed is:

1. A sampling system for solid materials comprising:
a sampling/feeding means to sample solid materials as continuously manufactured by a compression molding machine at fixed intervals and to feed said sampled materials, said sampling/feeding means including a damper having a balance weight to weigh a fixed amount of solid materials;
a transport gas control means to reciprocate a transport plug by executing either a feed or a suction mode;
a transport pipe having an inlet to receive said sampled materials from said sampling/feeding means and connected to said transport gas control means at the initial end thereof and to a material receiver of an inspecting station at its terminal end; and
said transport plug disposed in said pipe under said sampling inlet, as a stand-by position, said plug being pneumatically transported while keeping said sampled materials at a low speed into a terminal position in proximity to said inspecting station from said stand-by position when said gas control means is set inn a feed mode, and then being returned to said stand-by position from said terminal position after being transferred into the terminal position in said pipe when said gas control mans is set in a suction mode.

2. A method of sampling solid materials by executing following steps repeatedly at fixed intervals comprising:
weighing a fixed amount of solid materials for sampling continuously manufactured from a compression molding machine;
feeding a fixed amount of sampled solid materials between the bodies of a transport plug disposed in a stand-by position of a transport pipe;
pneumatically transferring said sampled materials into an inspecting station by said transport plug at a low speed in said transport pipe from its stand-by position to a terminal position by the use of pressurized gas, said sampled materials being kept between the bodies of transport plug;
receiving said sampled materials in a receiver of said inspecting station by dropping the materials kept between the bodies of said plug under substantially gravitational fall;
after completing transportation of said sampled materials, returning only said transport plug left at said terminal position to said stand-by position through said transport pipe by a suction operation of gas control means.

3. A method of sampling solid materials as set forth in claim 2, wherein said transport plug left at the terminal position is returned too said stand-by position by injecting pressurized gas toward the initial end of pipe by the use of an air purge unit disposed at a terminal end side of said terminal position while the initial end side of said stand-by position is open at a Atmosphere.

4. A sampling system for solid materials comprising:
a sampling/feeding means to sample solid materials as continuously manufactured by a compression molding machine at fixed intervals and to feed said sampled materials, said sampling/feeding means including a conic valve having a valve control means too control the insertion of solid materials; said sampling/feeding means including a damper having a balance weight to weigh a fixed amount of solid materials;
a transport gas control means to supply transport gas;
a transport pipe having an inlet to receive sampled materials from said sampling/feeding means and connected to said transport gas control means at the initial end thereof and to a material receiver of an inspecting station at its terminal end;
a means to open said transport pipe into atmosphere, provided at initial end side of plug housing portion constituting a stand-by position of said transport plug;
an air purge unit to inject pressurized gas provided at terminal end side of the terminal position of transport plug in said transport pipe, said air purge unit including a projectable air injection pipe which is housed while said transport plug is pneumatically transported and is projected when said plug is returned; and said transport plug disposed in said pipe under said sampling inlet, as a stand-by position, said plug being pneumatically transported while keeping said sampled materials between the bodies thereof at a low speed into a terminal position in proximity to said inspecting station from said stand-by position by the use of pressurized gas, and then being returned to said stand-by position from said terminal position after being transferred into the terminal position in said pipe by means of said air purge unit.

5. A sampling system for solid materials as set forth in claim 4, wherein said degassing holes are further provided at the upper wall of the end of said transport pipe which is connected to said material receiver.

* * * * *

UNITED STATES PATENT AND TRADEMARK OFFICE
CERTIFICATE OF CORRECTION

PATENT NO. : 5,056,962
DATED : October 15, 1991
INVENTOR(S) : Kiyoshi Morimoto, et al.

It is certified that error appears in the above-identified patent and that said Letters Patent is hereby corrected as shown below:

Title page,

Item [75] Inventors: Add two names and cities of inventors to appear as follows --KIYOSHI MORIMOTO, MISHIMA; AKIKAZU IWAMOTO; KATSUYA WATANABE, BOTH OF SUNTO; MASAHIKO SHIMIZU, MISHIMA; MASUO MORIYAMA, NUMAZU; TOMIRO ARAI; JUNJI NAKAGAWA, BOTH OF HIRAKATA, ALL OF JAPAN--

Signed and Sealed this

Ninth Day of May, 1995

Attest:

BRUCE LEHMAN

*Attesting Officer*     *Commissioner of Patents and Trademarks*